(12) United States Patent
Mandava et al.

(10) Patent No.: US 10,309,945 B2
(45) Date of Patent: Jun. 4, 2019

(54) SYSTEM, METHOD, AND APPARATUS FOR TEMPERATURE MONITORING AND VISIBILITY

(71) Applicant: Inteligistics, Inc., Pittsburgh, PA (US)

(72) Inventors: Panduranga Rao Mandava, Pittsburgh, PA (US); Erick John Muriungi Kithinji, Pittsburgh, PA (US); Narayana Ponnaganti, Pittsburgh, PA (US)

(73) Assignee: Inteligistics, Inc., Pittsburgh, PA (US)

( * ) Notice: Subject to any disclaimer, the term of this patent is extended or adjusted under 35 U.S.C. 154(b) by 493 days.

(21) Appl. No.: 14/691,964

(22) Filed: Apr. 21, 2015

(65) Prior Publication Data

US 2015/0300887 A1  Oct. 22, 2015

Related U.S. Application Data

(60) Provisional application No. 61/982,113, filed on Apr. 21, 2014.

(51) Int. Cl.
*G01K 1/02* (2006.01)
*G01N 33/02* (2006.01)

(52) U.S. Cl.
CPC ............. *G01N 33/02* (2013.01); *G01K 1/024* (2013.01); *G01K 1/026* (2013.01); *G01K 2207/04* (2013.01)

(58) Field of Classification Search
CPC ............ G01K 1/02; G01K 1/08; G01K 13/00; G01K 1/024; G01K 1/026; G01K 2207/04; G01N 33/02
See application file for complete search history.

(56) References Cited

U.S. PATENT DOCUMENTS

| 8,230,005 | B2 | 7/2012 | McKay et al. | |
| 2005/0178144 | A1* | 8/2005 | Crisp, III | B67D 1/0057 |
| | | | | 62/389 |
| 2006/0213904 | A1* | 9/2006 | Kates | B65D 79/02 |
| | | | | 219/702 |
| 2007/0062206 | A1* | 3/2007 | Brock | B60H 1/00978 |
| | | | | 62/129 |
| 2009/0303052 | A1* | 12/2009 | Aklepi | G06Q 10/08 |
| | | | | 340/573.2 |
| 2010/0100327 | A1* | 4/2010 | Jensen | G01D 9/005 |
| | | | | 702/2 |
| 2010/0127881 | A1* | 5/2010 | Schechter | H05K 7/20836 |
| | | | | 340/584 |

(Continued)

*Primary Examiner* — Stephanie E Bloss
(74) *Attorney, Agent, or Firm* — The Webb Law Firm

(57) ABSTRACT

The present invention relates to a system, method, and apparatus for monitoring temperatures of food products. The system includes a temperature sensor and at least one server computer. The temperature sensor includes at least one processor, a sensor probe adapted for insertion in a food product, and a wireless transmitter, where the temperature sensor programmed or configured to sense temperature data for the food product, and wirelessly transmit the temperature data. The at least one server computer is programmed or configured to receive the temperature data wirelessly transmitted by the temperature sensor, and generate at least one user interface based at least partially on the temperature data.

27 Claims, 15 Drawing Sheets

(56) References Cited

U.S. PATENT DOCUMENTS

| | | | | |
|---|---|---|---|---|
| 2011/0301903 A1* | 12/2011 | Humbert | G01D 18/008 | 702/104 |
| 2013/0067375 A1* | 3/2013 | Kim | F25D 29/00 | 715/769 |
| 2013/0227971 A1* | 9/2013 | Tamborra | F25D 29/006 | 62/62 |
| 2014/0041532 A1* | 2/2014 | Minvielle | A23L 3/001 | 99/468 |
| 2014/0041533 A1* | 2/2014 | Minvielle | A23B 4/00 | 99/486 |
| 2014/0313055 A1* | 10/2014 | Warkentin | H04Q 9/00 | 340/870.16 |
| 2015/0192475 A1* | 7/2015 | Eisenstadt | G01K 1/02 | 340/870.17 |
| 2015/0260699 A1* | 9/2015 | Minvielle | G01N 33/02 | 426/231 |
| 2015/0355036 A1* | 12/2015 | Giorgi | H04L 12/2825 | 702/130 |
| 2016/0178440 A1* | 6/2016 | Uno | G01J 5/0025 | 356/43 |
| 2016/0213053 A1* | 7/2016 | Frehn | G01N 33/02 | |

* cited by examiner

|  | Left Row Sensors | |
|---|---|---|
|  | Left Middle | Left Front |
| Time @ 33.5 F | 1:43:30 PM | 2:02:30 PM |
| Switched @ | 2:18:30 PM | 2:18:00 PM |
| Savings (minutes) | 35 | 15.5 |
| Row Avg (minutes) | 25.3 | |
|  |  |  |
| Time @ 33.5 F | 2:50:00 PM | 2:48:00 PM |
| Moved @ | 3:07:00 PM | 3:04:00 PM |
| Savings (minutes) | 17 | 16 |
| Row Avg | 16.5 | |
|  |  |  |
| Total Avg Row "lag time" | 41.8 minutes | |

FIG. 5B

SYSTEM, METHOD, AND APPARATUS FOR TEMPERATURE MONITORING AND VISIBILITY

CROSS REFERENCE TO RELATED APPLICATION

This application claims the benefit of U.S. Provisional Application No. 61/982,113, filed Apr. 21, 2014, the entire disclosure of which is hereby incorporated by reference in its entirety.

BACKGROUND OF THE INVENTION

Field of the Invention

This invention relates generally to temperature monitoring and, in particular, to a system, method, and apparatus for monitoring and visualizing temperatures in food products.

Description of Related Art

Typically, the temperature of food products, such as the pulp-temperature of fresh produce or food stored for retail sales, is measured with a temperature sensor that is manually inserted into a food product when pallets are in pre-cooling or cold storage warehouses, during transport or retail store shelves. Such methods require labor to regularly check the temperatures to determine when a food product must be cooled or heated to bring temperatures to an acceptable level or moved to a location having a different temperature. When fresh produce is harvested, it should be quickly cooled to a low temperature (e.g., 32° F. for certain fruits and vegetables) in order to enhance quality and extend shelf life and freshness. Manual temperature probing under these circumstances are especially inefficient and problematic when manual temperature probing techniques are used. A manual approach results in decreased throughput of food products and increased costs and potentially lower quality and depleted shelf life and freshness. Likewise, humidity of the environment of the enclosure where the food resides has certain effects on food products.

SUMMARY OF THE INVENTION

Accordingly, and generally, provided are improved systems, methods, and apparatuses for temperature and/or humidity monitoring and visibility that address or overcome certain drawbacks and deficiencies in existing systems and processes.

According to a preferred and non-limiting embodiment of the present invention, provided is a system for monitoring temperature of food products, including: a temperature sensor comprising at least one processor, a sensor probe adapted for insertion in a food product, and a wireless transmitter, the temperature sensor programmed or configured to sense temperature data for the food product, and wirelessly transmit the temperature data; and at least one server computer configured to receive the temperature data wirelessly transmitted by the temperature sensor, and generate at least one graphical user interface based at least partially on the temperature data.

According to another preferred and non-limiting embodiment of the present invention, provided is a wireless apparatus for monitoring temperature of food products, including: a waterproof or water resistant housing; at least one sensor probe; a wireless transmitter positioned within the housing; and at least one processor positioned within the housing and in communication with the at least one sensor probe and the wireless transmitter, the at least one processor configured to determine temperature data based on data received from the at least one sensor probe, and wirelessly transmit the temperature data to a receiving device using the wireless transmitter.

According to a further preferred and non-limiting embodiment of the present invention, provided is a method for monitoring food product temperatures, including: receiving, from a plurality of temperature sensors, temperature data over a wireless network, wherein the plurality of temperature sensors are adapted for insertion into a food product, and wherein the temperature data comprises a pulp-temperature of the food product; storing the temperature data in at least one data structure; and generating data configured to display, on at least one user computer, a graphical user interface based at least partially on the temperature data.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

FIG. 5B depicts lag time calculations for the data shown in FIG. 5A according to the principles of the present invention;

DETAILED DESCRIPTION OF THE INVENTION

Figure 1:
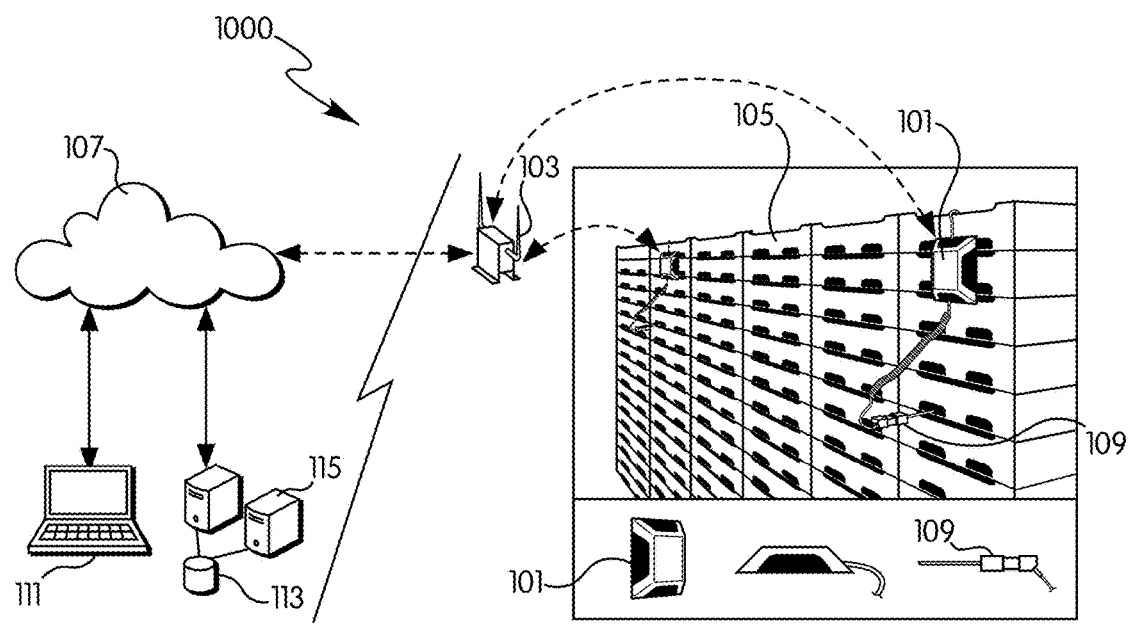
FIG. 1 depicts a schematic diagram of a system for monitoring temperatures of food products according to the principles of the present invention.

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or device to be in communication with another unit or device means that the one unit or device is able to receive data from and/or transmit data to the other unit or device. A communication may use a direct or indirect connection, and may be wired and/or wireless in nature. Additionally, two units or devices may be in communication with each other even though the data transmitted may be modified, processed, routed, etc., between the first and second unit or device. For example, a first unit may be in communication with a second unit even though the first unit passively receives data, and does not actively transmit data to the second unit. As another example, a first unit may be in communication with a second unit if an intermediary unit processes data from the first unit and transmits processed data to the second unit. It will be appreciated that numerous other arrangements are possible.

As used herein, the term "food product" may refer to one or more food items such as, for example, produce (e.g., fruits and vegetables), meat products (e.g., cooked meats, raw meats, etc.), and/or any other like products that may be perishable and/or affected by temperature. As used herein, the terms "cooling container" and "container" may refer to any container, room, or chamber that is used to cool food products, including those that use vacuums or fans to remove heat, and may or may not use coolants. It will be appreciated that the present invention contemplates the use of various types of cooling containers and methods, including but not limited to forced air cooling, vacuum tube cooling, and various forms of cold storage.

In a preferred and non-limiting embodiment of the present invention, provided is a system and method for monitoring the temperatures of one or more food products. Preferably, pulp-temperatures of food products are monitored, although it will be appreciated that an external temperature or proximate temperature may also be measured and monitored. The temperatures are measured with wireless temperature sensors, and other measurements (e.g., humidity, pressure, carbon dioxide, oxygen, ethylene, microbial elements, and/or the like) may be provided by additional sensors. The temperatures can be monitored to determine when food products should be moved. For example, in a non-limiting embodiment, the present invention may be used to monitor temperatures of food products in a pre-cooling container or facility, such as a vacuum tube/tunnel. Temperatures may also be monitored in other cooling containers, including primary cooling containers, freezers, reefer truck trailers, reefer 20-foot or 40-foot multi-modal containers, and/or the like. The humidity of a cooling container and other environmental factors may also be monitored. The wireless temperature sensors are configured to transmit temperature data, such as raw temperature measurements, calculated temperature readings, humidity measurements, and/or the like. As used herein, the term "temperature data" refers to any type of data relating to or associated with temperature including, but not limited to, raw temperature, calculated temperature, and measurements of pressure, humidity, carbon dioxide, oxygen, ethylene, microbial elements, and/or other environmental factors that can affect food products in a similar way as the temperature or are related to temperature. A receiving device, such as a computer, gateway, or range extender, receives the wireless signals from the temperature sensors and communicates the temperature data to one or more databases. The temperature data is then used to generate one or more graphical user interfaces to display the data, generate reports and/or visualizations, generate and/or display alerts, and for other purposes.

The system and method for monitoring the temperatures of one or more food products as described herein allows for a facility to maximize the throughput of heat-sensitive food products, such as produce. The system also reduces or eliminates the need to take manual pulp-temperature readings, minimizes the number of punctures in the food products from pulp-temperature readings, improves product shelf life, ensures higher quality food products, and saves costs on energy and labor.

Referring now to FIG. 1, a system 1000 for monitoring the temperatures of one or more food products is shown according to a preferred and non-limiting embodiment of the present invention. A temperature sensor 101 is shown mounted to a pallet 105 including food products. The temperature sensor 101 includes a sensor probe 109, which is inserted at least partially into a food product. The sensor probe may be a needle puncture probe, although other types of probes may also be used. The temperature sensor 101 is in wireless communication with a gateway device 103, which in turn communicates with a network environment 107 such as, but not limited to, the internet or a local area network (LAN). The temperature sensor 101 may transmit temperature data in real-time, or at specified intervals (e.g., every 30 seconds, every minute, at a configurable interval, etc.). In non-limiting examples, the temperature sensor 101 may be configured to obtain measurements with the highest precision possible by using a variety of sensor technologies to generate or obtain the desired level of accuracy and precision. Further, in non-limiting embodiments, the sensor probe 109, additional probe(s), or other like sensor arrangements may be used for sensing humidity, carbon dioxide, oxygen, ethylene, microbial elements, and/or other environmental parameters, and the temperature sensor and other similar sensors 101 may transmit humidity information and other measurements as part of the temperature data.

Still referring to FIG. 1, a server 115 in communication with a database 113 or other like data structure is in communication with the network environment 107. The server 115 may be a web server or other like network server, and may be configured to store the temperature data received from the gateway device 103 in the database 113. The server 115 may provide "cloud-based" services, including but not limited to access to the temperature data and remote control of or interaction with the temperature sensors. The temperature data may be provided and/or stored in any number of forms, such as but not limited to Extensible Markup Language (XML). The use of XML format data, or other like formats, enables ease of access to and interaction with the data. The server 115 may be local or remote to the database 113. A user computer 111 is also in communication with the network environment 107 and is configured to request, retrieve, and/or display the temperature data that is stored on the database 113.

With continued reference to FIG. 1, it will be appreciated that one or more range extending devices (not shown) may be used to facilitate communication between the temperature sensor 101 and the gateway device 103. Moreover, it will be appreciated that the gateway device 103 may be one of several different networking devices. For example, the gateway device 103 may be a wireless modem, a computer already in communication with the network environment 107, a mobile device, or any other like device capable of receiving data and transmitting data to a location on a network.

Still referring to FIG. 1, the temperature sensor 101 may wirelessly communicate with the gateway device 103 via any appropriate communication protocol. In a preferred and non-limiting embodiment, a low-energy ZigBee protocol is used. However, it will be appreciated that any suitable wireless communication protocol may be used. In some examples, the temperature sensor 101 communicates directly with the gateway device 103 or indirectly through one or more range extending devices (not shown). Additionally, in some non-limiting embodiments, a plurality of temperature sensors 101 may communicate with one another in a mesh-type network. This type of arrangement allows for a temperature sensor 101 in the mesh network that is most proximate to the gateway device 103 to relay signals propagated from other, further positioned, temperature sensors 101. Various other arrangements are possible.

In a preferred and non-limiting embodiment, the temperature sensors 101 include one or more batteries to power the electronic components. Through the use of low-energy communication protocols, such as but not limited to ZigBee, low-energy Bluetooth, and the like, the battery life can be extended. Moreover, the temperature sensor 101 may have a reduced-energy or sleep mode that reduces use of the batteries. The reduced-energy or sleep mode may be initiated at times between scheduled or specified measurements and communications. For example, if the temperature data is updated once per minute, the temperature sensor 101 may be in a reduced energy or sleep mode and, when a minute passes, exit the reduced energy or sleep mode and take a temperature measurement and communicate the resulting temperature data to the gateway device 103. After communicating the temperature data, the temperature sensor 101 may return to the reduced energy or sleep mode.

With continued reference to FIG. 1, the temperature sensor 101 may include a housing. In a preferred and non-limiting embodiment, the housing of the temperature sensor 101 is waterproof, water resistant, moisture proof, and/or otherwise insulated or protected to allow for use in different environmental conditions. The housing may also include insulation or other materials to protect the internal electronics from extreme temperatures to which the sensor 101 may be exposed. Additionally, the housing of the temperature sensor 101 may contain a processor, such as a microprocessor, central processing unit, or other like processing device. The processor may be part of a microcontroller, which includes memory, or may be in communication with external memory. The memory contains software for performing tasks such as, for example, interacting with the wireless transmitter, converting sensor data into temperature values, entering or existing a sleep mode, generating alerts, and/or the like. The memory may also store, for example, an identifier for the temperature sensor 101 and a location. The housing also includes a wireless transmitter configured to wirelessly transmit signals to a receiving device, such as but not limited to the gateway device 103. The housing may additionally include an attachment arrangement, such as one or more hooks, for attaching the temperature sensor 101 to a box, pallet, wall, or other surface. Using an attachment arrangement, the temperature sensor may be hung on a wall or other surface near the container for subsequent use. Other arrangements are possible, and additional devices such as a Global Positioning System (GPS) receiver, cellular or satellite modem, and/or other like devices may also be included.

The temperature sensors 101 may be arranged in various ways with respect to the food products and/or pallets. For example, two sensors may be used per row, with one sensor placed near the end of a row of pallets and another sensor placed on the inside of the tunnel at the middle of the row. Numerous variations are possible, using different placement locations, a different number of sensors, and/or the like. Further, the temperature sensors 101 may be calibrated and/or configured remotely through use of the system 1000.

Figure 2:
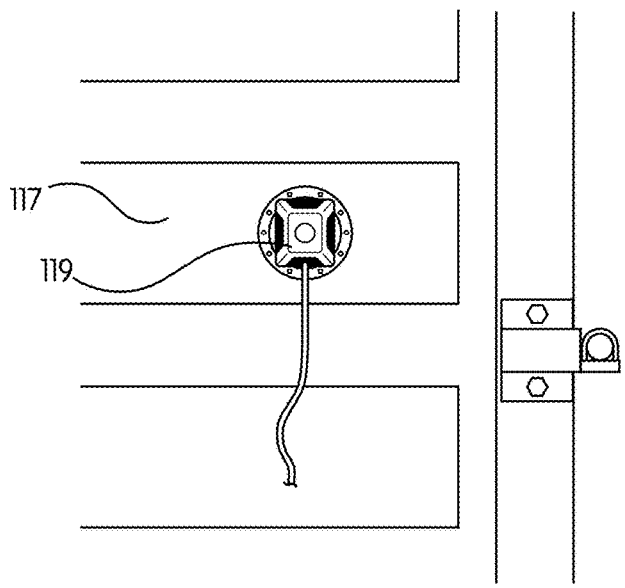
FIG. 2 depicts an arrangement of a range extending device on a cooling container according to the principles of the present invention.

Referring now to FIG. 2, a cooling container 117 with a range extending device 119 is shown according to a preferred and non-limiting embodiment. The range extending device 119 may be a repeater or other like network device that is capable of receiving wireless signals from the temperature sensor 101 (as shown in FIG. 1) or from other range extending devices, and relay those signals to the gateway device 103 (as shown in FIG. 1). The construction of many cooling containers 117, including pre-cooling vacuum tubes, often impede the passage of signals. This problem may be solved by placing the range extending device 119 on a particular part of the container 117. As shown in FIG. 2, the range extending device 119 is placed on an exterior portal window of the container 117. With such a placement, the signals from inside can be received through the glass or other material used in the portal window. It will be appreciated that a range extending device 119 may be placed anywhere inside or outside of a cooling container 117 such that it can receive signals from the temperature sensor 101 and relay the signals elsewhere.

In some non-limiting examples, multiple range extending devices may be used to establish communication between the temperature sensor 101 and the gateway device 103. Optimal placement locations of the range extending device 119 in non-limiting embodiments may also include, for example, a position proximate to a door gasket on the interior or exterior of a cooling container. Further, an antenna for the gateway device 103 or the range extending device 119 may be placed inside the cooling container through the door gasket or through some other opening. The antenna may be enclosed in an armored or otherwise protected cable that is able to withstand the pressure of the door gasket when it is closed.

Referring now to FIG. 1, the server 115 may include one or more processors and, as previously explained, may be a web server or other like network server. In a preferred and non-limiting embodiment, the server is configured to provide graphical user interfaces to one or more user computers 111 via a network environment 107. The Hypertext Transfer Protocol (HTTP) or other like protocols may be used to provide user interfaces to user computers 111, such as desktops, laptops, and mobile devices, through a software application installed on the user computers 111. For example, the server 115 may provide webpages via HTTP to web browsers executing on user computers 111. The software application may also include, for example, a mobile application (e.g., for Android, iOS, Windows, or the like), and/or any other client-side software platform configured to communicate with a network and generate a display based on received data.

Figure 3A:
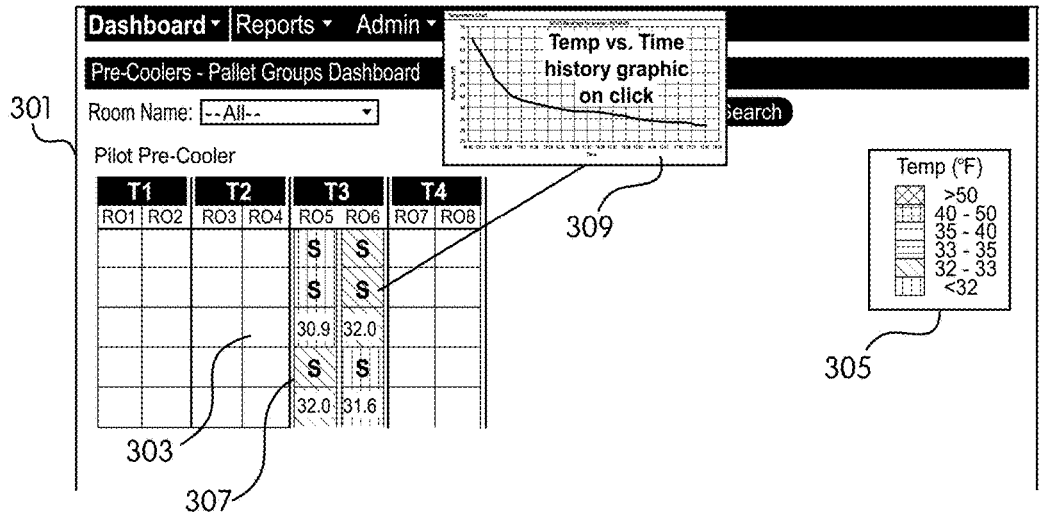
FIGS. 3A-3H depict graphical user interfaces according to the principles of the present invention.
Figure 3B:
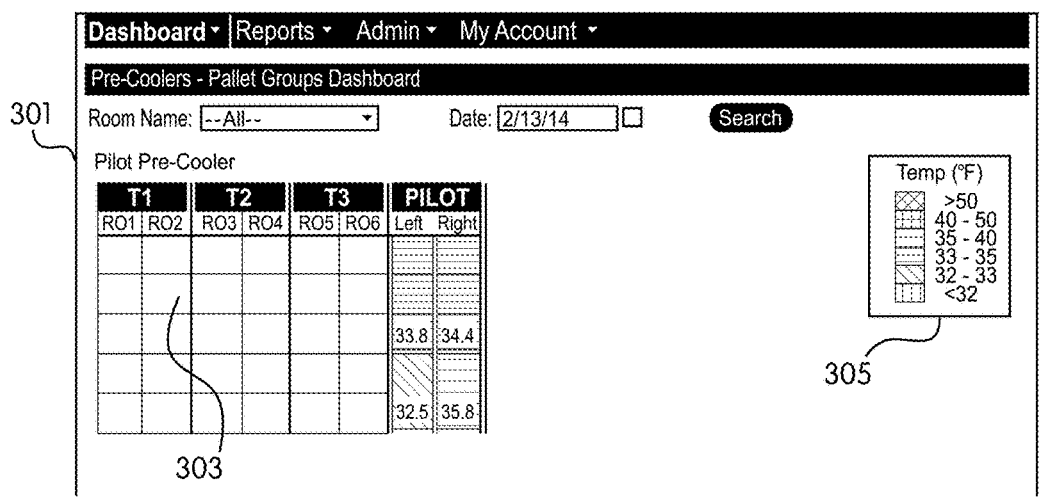
Figure 3C:
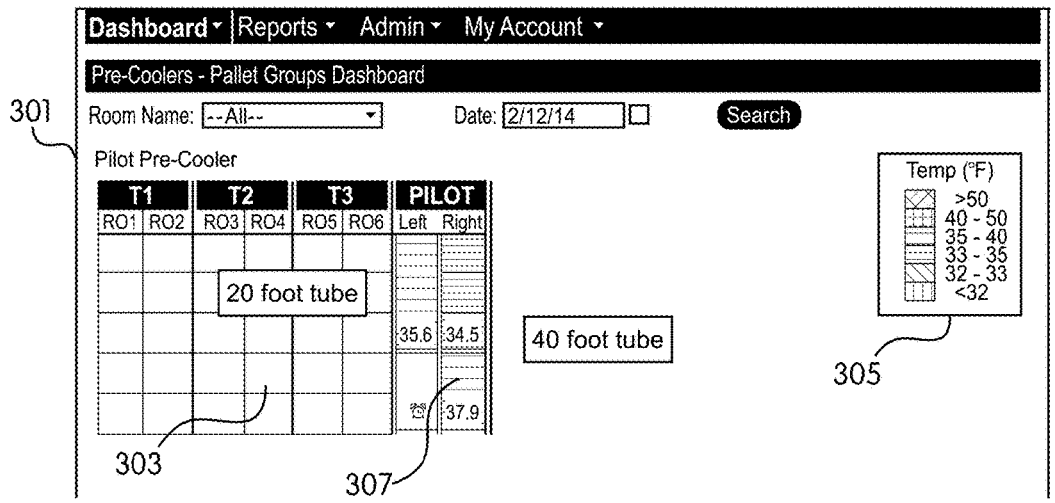
Figure 3D:
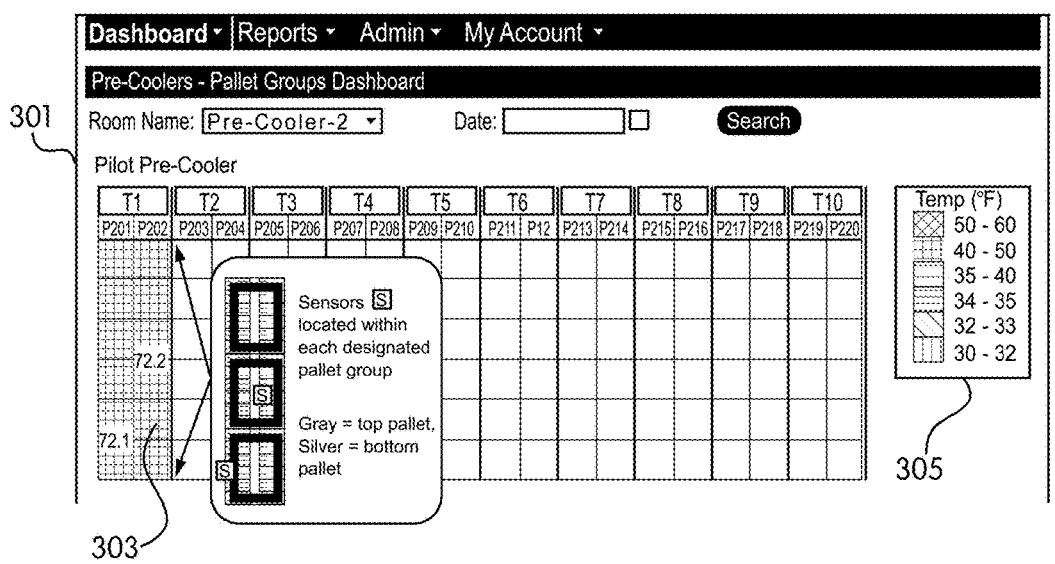

Referring now to FIGS. 3A-3F, graphical user interfaces are shown according to preferred and non-limiting embodiments. A dashboard interface 301 provides selectable options such as, but not limited to, drop-down menus, radio buttons, checkboxes, input fields, buttons, links, and/or the like. Through the selectable options, a user may choose how to view the temperature data. For example, a visual representation of available cooling containers 303 may be shown. In the illustrated example, the cooling containers 303 are pre-cooling vacuum tunnels/tubes displayed laterally on the interface 301. Visualizations of the food products or pallets 307 containing the food products may also be displayed. The temperature of each food product or pallet 307 may be displayed on the visual representation, or may be displayed in response to a user action such as a mouse-over event, a click-event, and/or the like. The humidity of each cooling container 303 and/or other measurements may also be displayed. An icon or other visual representation may also be displayed to represent a particular pallet 307, or group of pallets on which a sensor is placed. For example, referring to FIG. 3D, a sensor icon ("S" in a box) is shown within each designated pallet group. Top and bottom pallets may also be distinguished based on color, as shown in FIG. 3D.

Figure 3E:
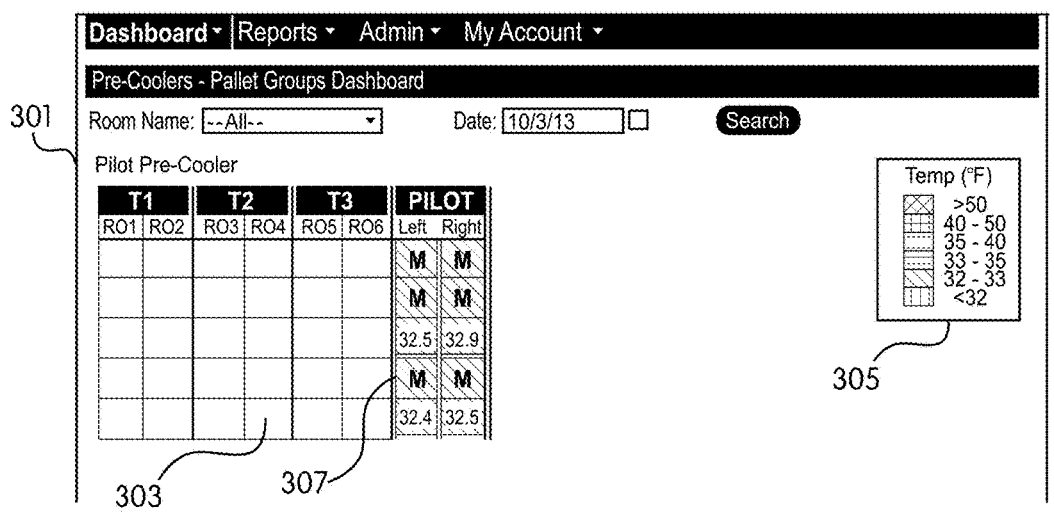

In preferred and non-limiting embodiments, other visual indicators may be used to convey information to users. For example, with reference to FIG. 3A, the pallets 307 shown on the interface 301 have a letter "S" to indicate that pallets should be physically swapped. Various other icons and text may also be used. For example, when the temperature reaches a certain threshold (e.g., between 32 and 33° F.) the letter "S" or another visual representation may appear and the pallet may turn a particular color (e.g., green). The visual representation may blink or exhibit some other visual effect to attract users' attention. If the temperature falls below a threshold (e.g., less than 32° F.), the visual representation may also appear and the pallet may turn another color (e.g., red). A user of the system is thereby alerted to physically swap the pallets after removing the sensors and hanging them on the wall. The visual representation may change (e.g., from a blinking "S" to a static "5") once it is determined that the probes have been removed from the food products. With reference to FIG. 3E, the pallets 307 have a letter "M" to indicate that the pallets should be moved from the cooling container. Similar to the indicator for indicating that the pallets should be swapped, this visual representation may be displayed when the temperature reaches a move threshold or drops below a certain value. The visual representation may change (e.g., from a blinking "M" to a static "M") once it is determined that the probes have been removed.

Still referring to FIGS. 3A-3F, the dashboard interface 301 may include color-coded visual representations. In FIGS. 3A-3E, different hatch patterns represent different colors. However, it will be appreciated that various indicators may also be used to differentiate between visual representations displayed on the interfaces. As an example, the visual representation of the pallets 307 are shown in varying colors on the interface 301 based on the temperature of the particular pallet or food product in that pallet. A legend 305 may also be displayed on the interface 301 to associate different colors with different temperatures or temperature ranges. As shown in this non-limiting example, temperatures greater than 50° F. are represented by orange, temperatures between 40 and 50° F. are represented by yellow, temperatures between 35 and 40° F. are represented by light blue, temperatures between 33 and 35° F. are represented by dark blue, temperatures between 32 and 33° F. are represented by green, and temperatures less than 32° F. are represented by red. Of course, it will be appreciated that various ranges and colors may be used, and further, these ranges and colors may be configured by the user. In a non-limiting embodiment, a particular color (e.g., green) represents an optimal temperature at which the food product or pallet 307 should be moved to another location, such as a cooler, pre-cooler, or the like. The colors and/or ranges may be predefined and/or specified by a user through a user interface. Referring to FIG. 3E, a dashboard interface 301 is shown in which the food products being monitored have reached the threshold temperature or optimal temperature range and should be moved to another location (e.g., a location exhibiting a different temperature) to avoid over-cooling. As can be seen, the visual representation of the pallets 307 in FIG. 3E are all green in this non-limiting example. It will be appreciated that, in non-limiting embodiments, humidity information and other measurements may also be color coded for display on one or more user interfaces.

With continued reference to FIGS. 3A-3G, visual representations of the cooling containers 303 may be blank to indicate that the container is available for loading additional pallets. After the pallets have been physically loaded into the cooling containers, and the sensors placed on the pallets and the probes inserted into the food product, the system may detect that the probes were inserted. Various trigger events may be used to determine that a probe has been inserted into a food product. For example, if the food product temperature is above a certain value (e.g., 45° F.) in a cooling container having a colder ambient temperature, or changes a certain amount (e.g., 8° F.) from a previous measurement or a known ambient temperature, the system can determine that the probes have been inserted into the food product.

Figure 3F:
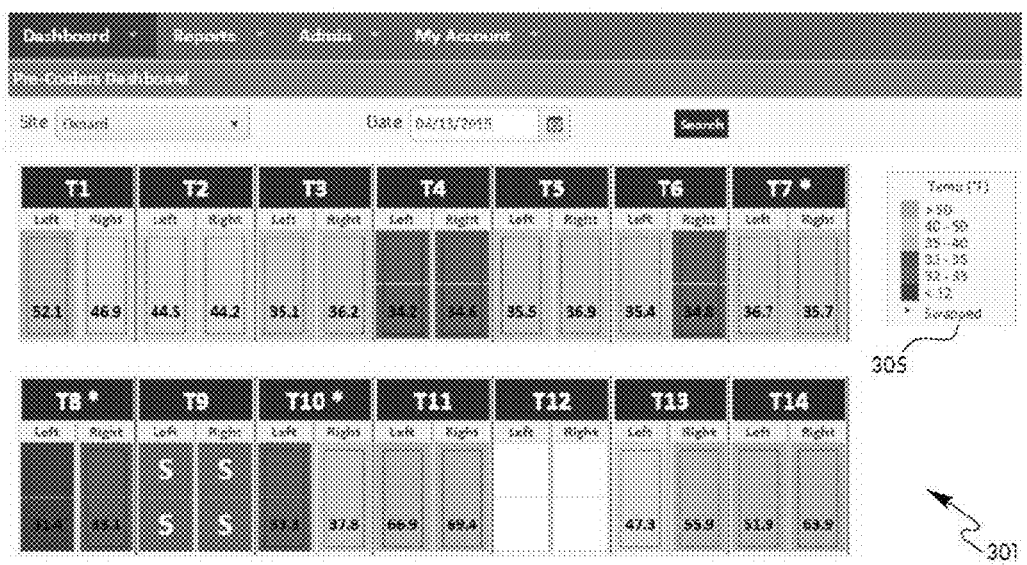
Figure 3G:
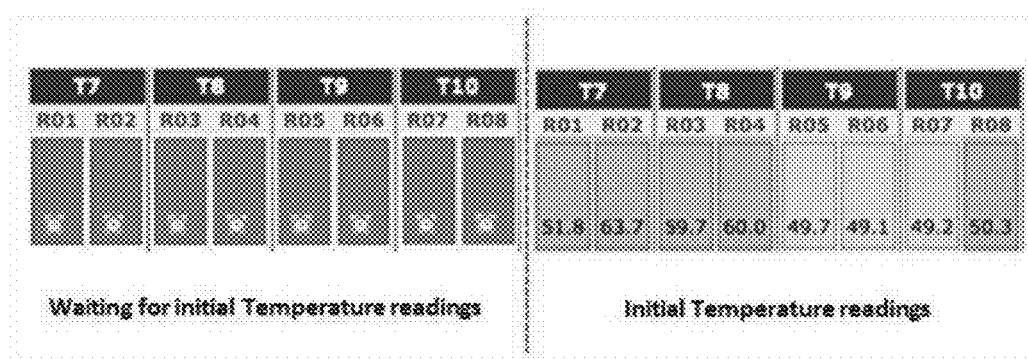
Figure 3H:
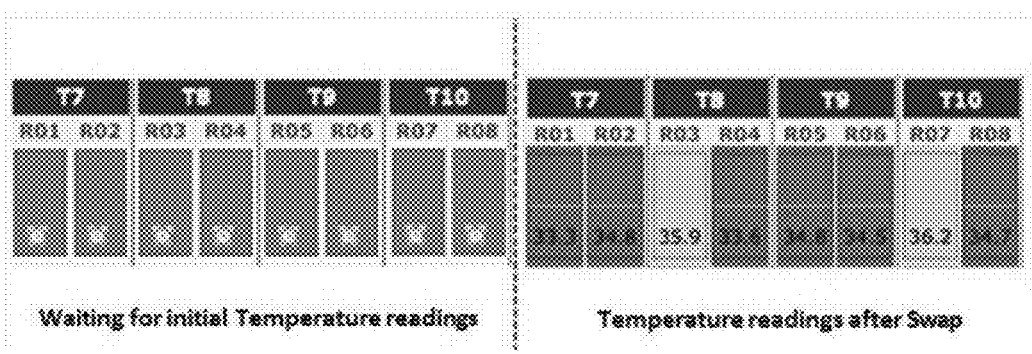

Referring now to FIGS. 3F and 3G, the visual representations of the cooling containers 303 may display icons, such as a clock or hourglass, as initial temperature readings are obtained. Once the initial temperature readings are obtained, the colors of the cooling containers 303 may then change based on the temperature and corresponding color code. FIG. 3F illustrates a sequence of interfaces that begins with waiting for initial temperature readings and then displaying the initial temperature readings by value and color code. FIG. 3G illustrates a sequence of interfaces that begins with waiting for initial temperature readings after pallets are swapped and then displaying the temperature readings after the swap occurs.

Figure 4A:
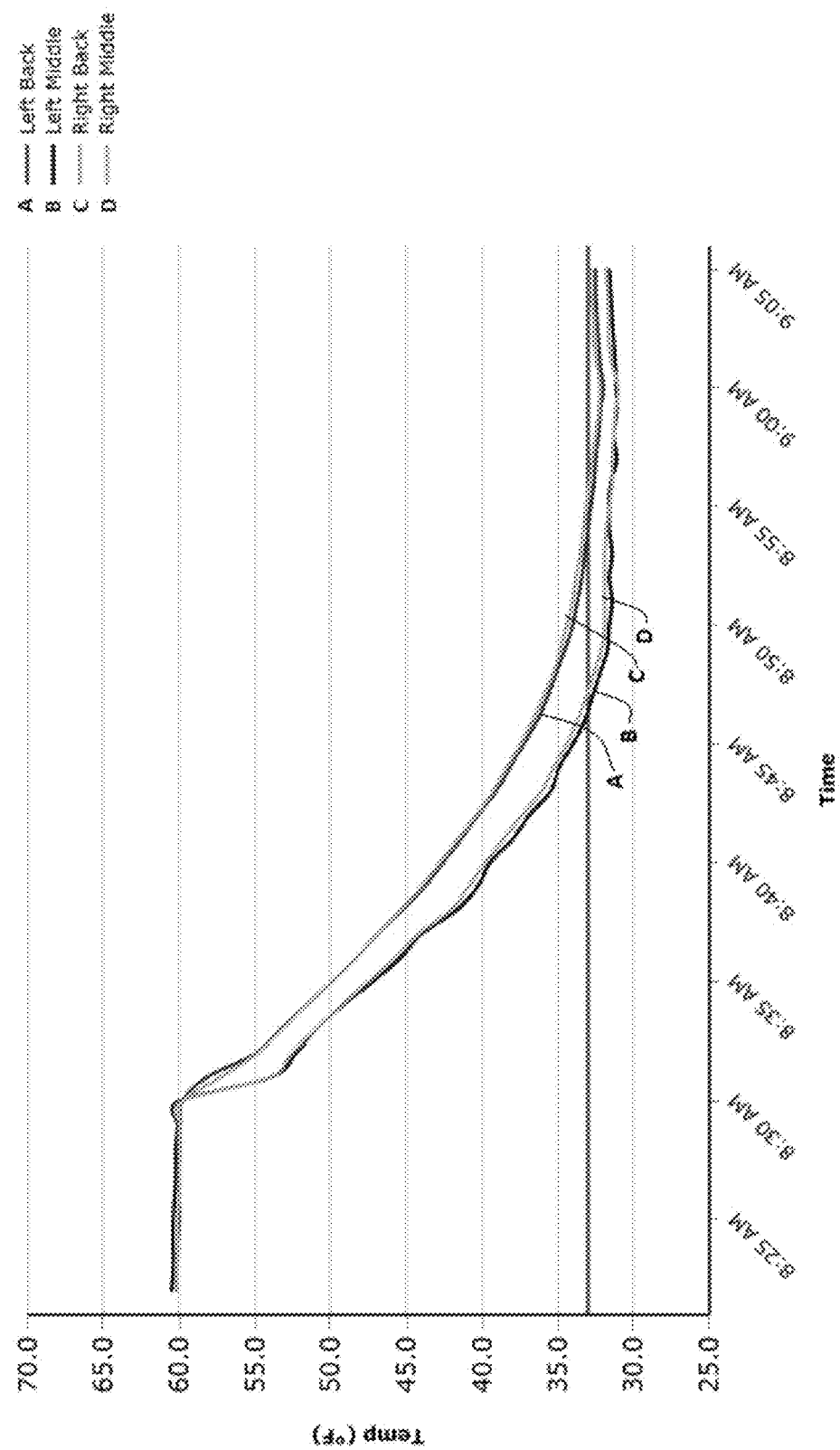
FIGS. 4A and 4B depict temperature charts according to the principles of the present invention.
Figure 4B:
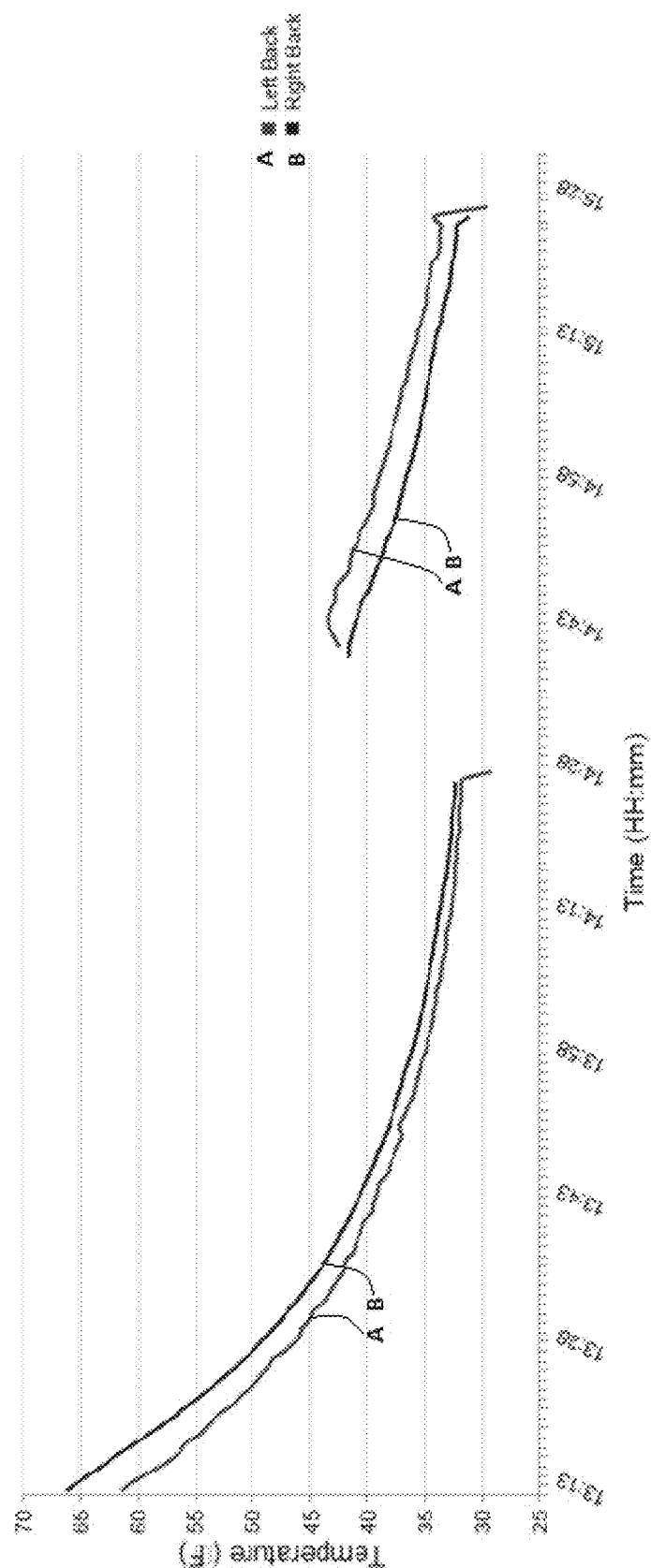

Referring to FIG. 3A, a chart 309 is shown representing temperature data over a period of time. Such a chart 309 may be generated by the server computer or client computer based on the temperature data and in response to a user request. For example, one or more selectable options may be provided to allow a user to configure or generate a chart 309 based on a particular food product, pallet, cooling container, and/or the like. Selectable options may also be used to specify a time period to be displayed by the chart. In some non-limiting embodiments, clicking or selecting a pallet or group of pallets may automatically generate and/or display a chart 309. FIGS. 4A and 4B illustrate further non-limiting examples of charts 309 illustrating temperatures over time.

Figure 5A:
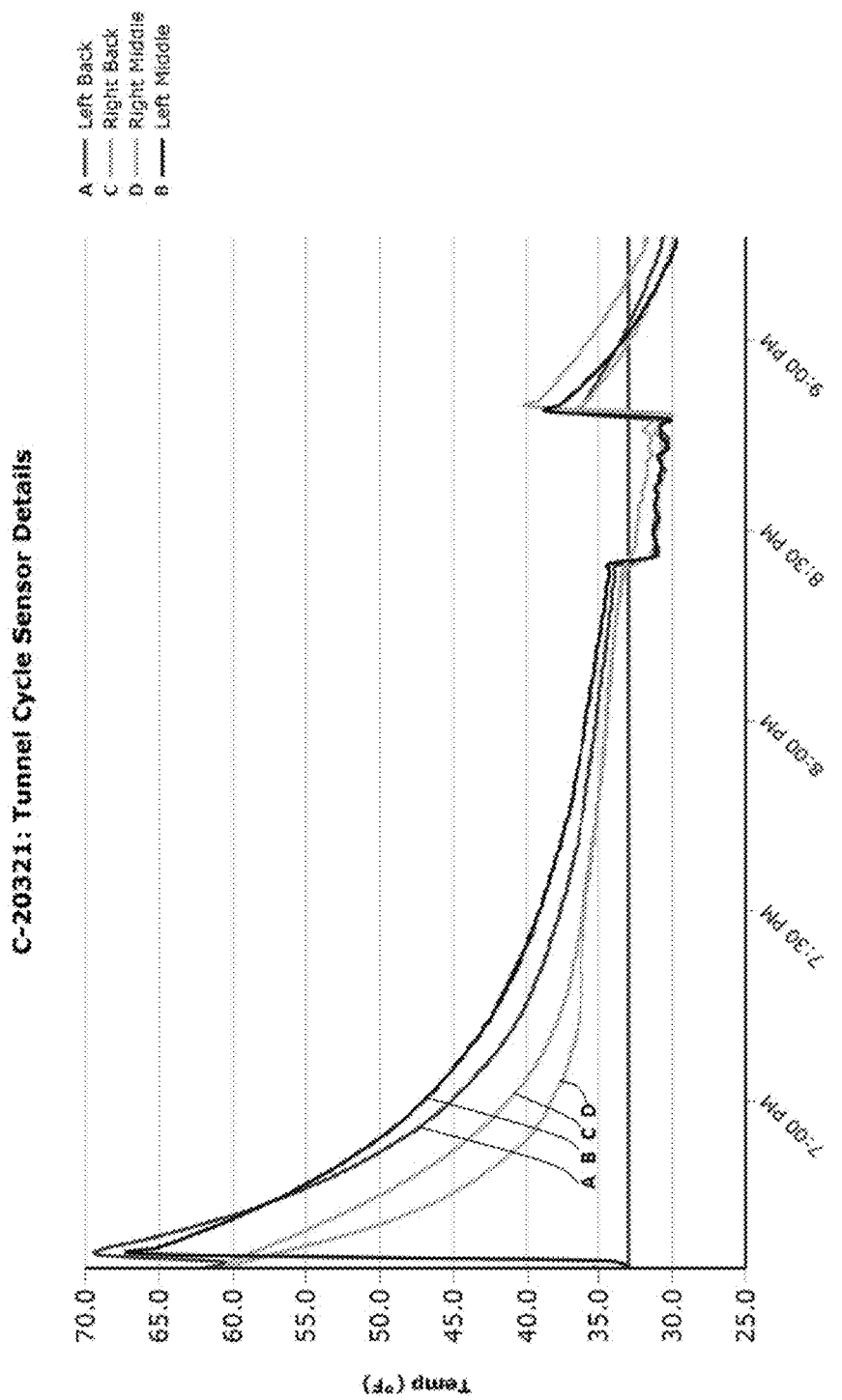
FIG. 5A depicts a chart showing temperatures of multiple pallets over time according to the principles of the present invention.

In a preferred and non-limiting embodiment, the temperature data displayed through the user interfaces 301 allow for personnel to be informed when containers, such as pallet tunnels (e.g., pre-coolers, reefer trailers, and multi-modal containers), reach a desired pulp-temperature. This allows the personnel to move the pallets accordingly, and therefore maximizes the throughput of the food products by reducing or eliminating the amount of unnecessary additional cooling time. The system 1000 may also monitor this cooler "lag time," measured from the time that a row or tunnel reaches a desired temperature to when the pallets in the tunnel are actually moved. A user interface 301 may display the lag time as a numerical value and/or visual chart. FIG. 5A illustrates a chart of temperature data over time according to a non-limiting embodiment. These temperature profiles indicate information to the operators relating to the stage of the cooling the container or pallet is in (e.g., getting close in time to switching or removal of the pallets to another location, when cooling rates are to be to changed, or, in the case of reefer trailers, when the temperature is above a required threshold temperature) without requiring any human interactions on computers to create these stages. Trigger events are indicated by changes in the chart profile. For example, significant changes can be seen at the beginning of the chart, before the 8:30 time mark, and after the 8:30 mark but before 9:00. A first trigger event may indicate the initial sensor placement. A second trigger event may occur when the pallets are to be swapped because the temperature reached a swap threshold. A third trigger event may occur after sensors are replaced following a swap event. A fourth trigger event may occur when the pallets are to be removed from a cooling container because the temperature reached a move threshold. FIG. 5B illustrates a lag time analysis for the temperature data shown in FIG. 5A that may be automatically generated by the system 1000 and displayed to a user through an interface. This data may also be used to determine a cost-savings generated through use of the system 1000.

In a preferred and non-limiting embodiment, an alert may be generated by the system 1000 in response to a temperature of a food product, pallet, or container reaching or exceeding a specified value. The alert may be displayed on a user interface and/or be transmitted via email, text message, push notification, automatic telephone call, and/or the like. The method of delivery for an alert may be configured or specified by a user through a user interface. Further, the alerts may be customized by a user to specify a subject line, message content, recipient, or the like. For example, an email alert may specify "P101 pallet groups now ready for removal." Business rules may be defined in various ways to allow customization of such alerts and message information. Alerts may also be based at least in part on humidity information. It will be appreciated that alerts may be generated by the server 115 and/or the temperature sensor 101. For example, software in the temperature sensor 101 may compare the measured temperatures with threshold values to determine if an action needs to be taken. In other examples, alerts may be generated by the server 115 by comparing the received temperature data to stored thresholds.

In non-limiting embodiments, various trigger events may cause alerts to be generated or changes to be made on the graphical user interfaces. Threshold values and/or ranges used by the trigger events may be specified by a user or predefined. For example, different values may be used based on products, facilities, cooling equipment, weather conditions, and/or the like. Temperature data and other information received from one or more sensors may also be used to determine if a trigger event has occurred. For example, a trigger event may occur if only all sensors are detecting a specified temperature or range and, in other examples, the temperatures and other values may be averaged for determining if a trigger event has occurred.

In a non-limiting embodiment, the temperature data may be monitored to determine if the probes have been removed from the food products. Various trigger events may be used to determine if a probe has been removed. For example, because the sensor will be detecting the ambient temperature of the cooling container when the probe is removed from the product, a trigger event may occur when a temperature reading is in a specific range (e.g., 32-33° F.), and the sensors detect a certain (e.g., 1 degree) temperature drop. Another trigger event may occur when a temperature reading is below a certain value (e.g., 32° F.) and the sensors detect a certain temperature drop (e.g., 0.5° F.). Another trigger event may occur based on multiple sensors all detecting temperatures below a certain value (e.g., 31.6° F.). Yet another trigger event may occur when a temperature rise is detected. For a temperature rise trigger event, the time difference between the initial placement of the sensor and the temperature rise may be considered. For instance, if the time difference between sensor placement and the temperature rise is greater than a certain value (e.g., 20 minutes) the temperature rise required to cause the trigger event may have to be a certain value (e.g., 3° F.). It will be appreciated that various other trigger events may be used to determine if a probe has been removed from a product.

According to a preferred and non-limiting embodiment, the system 1000 may be in communication with the control system for a fan and/or cooling system in place at a facility. In such examples, the graphical user interface may provide selectable options to allow a user to turn "on" or turn "off" such systems, to reduce power, or to otherwise control operation of the systems. Additionally, in non-limiting embodiments, the fan and/or cooling system may be controlled automatically based on the temperature data. For example, in response to a food product, pallet, or container reaching or exceeding a desired temperature, the fan and/or cooling system may be turned "off" or reduced in power. The lag time calculation discussed above may also be used to automatically control the fan and/or cooling system.

In a preferred and non-limiting embodiment, reports and analytic data may be generated and displayed based on current and/or historic temperature data. The content and parameters for such reports and analytics may be predefined, configured, and/or specified by a user through a graphical user interface. As an example, selectable options may be provided to allow a user to generate analytic reports by food product type, package type, date, time of day, container, location, and/or the like. Quality assurance and/or quality control charts may be generated to determine if cooling systems and/or containers are within operational specifications.

Figure 6:
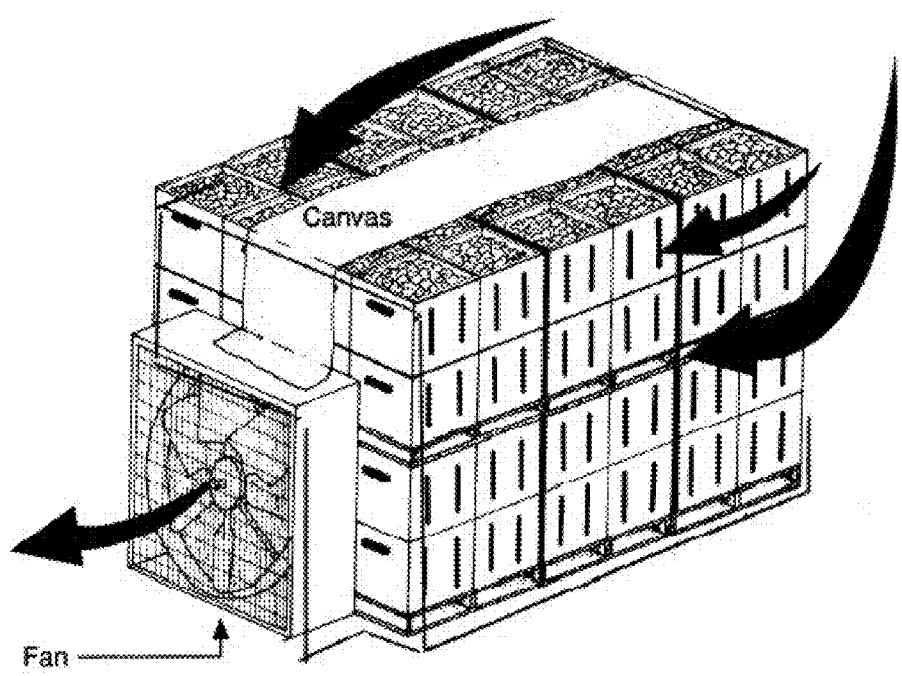
FIG. 6 depicts a pallet of food products according to the principles of the present invention.
Figure 7A:
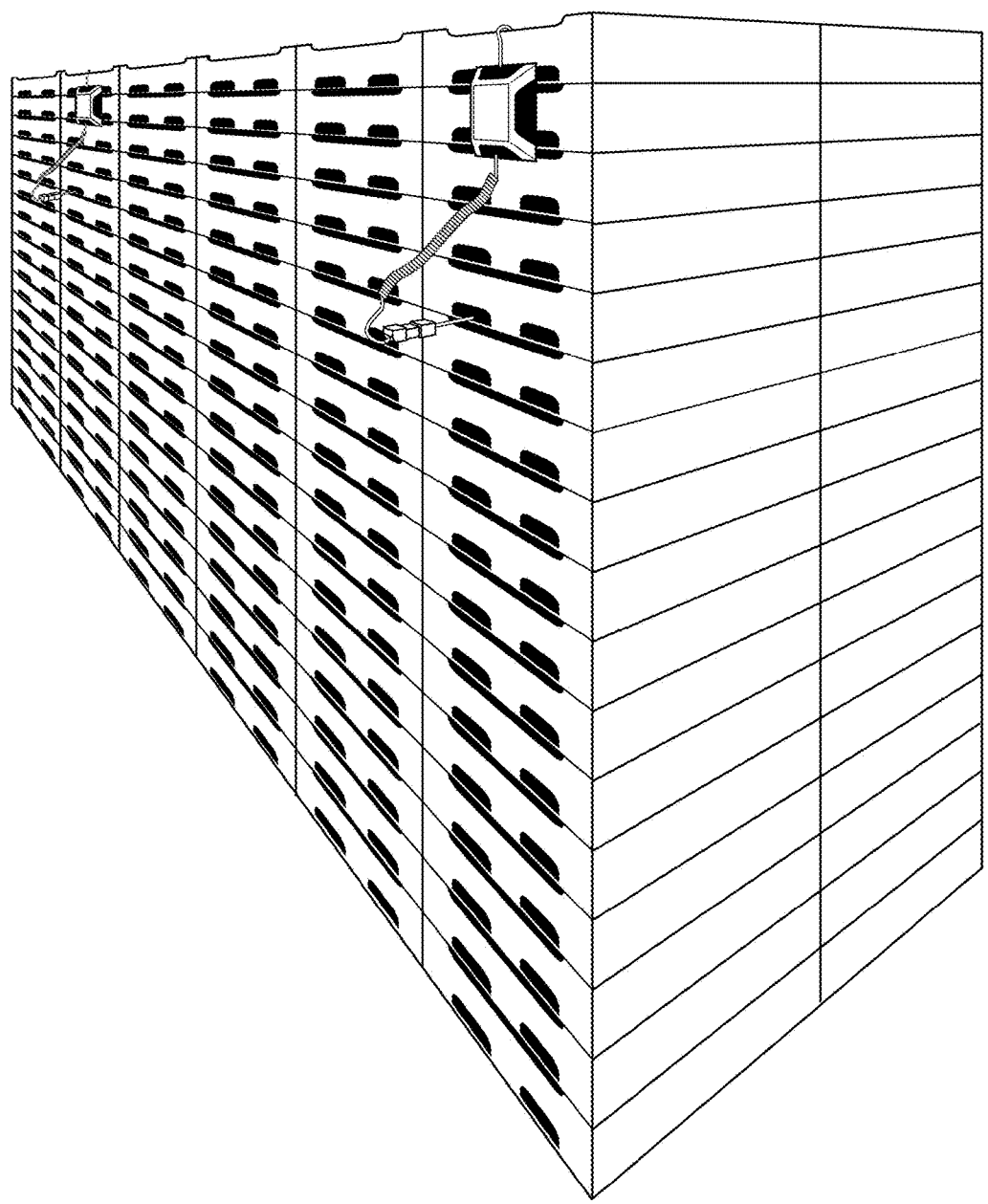
FIGS. 7A and 7B depict pallets of food products having temperature sensors mounted thereon according to the principles of the present invention.
Figure 7B:
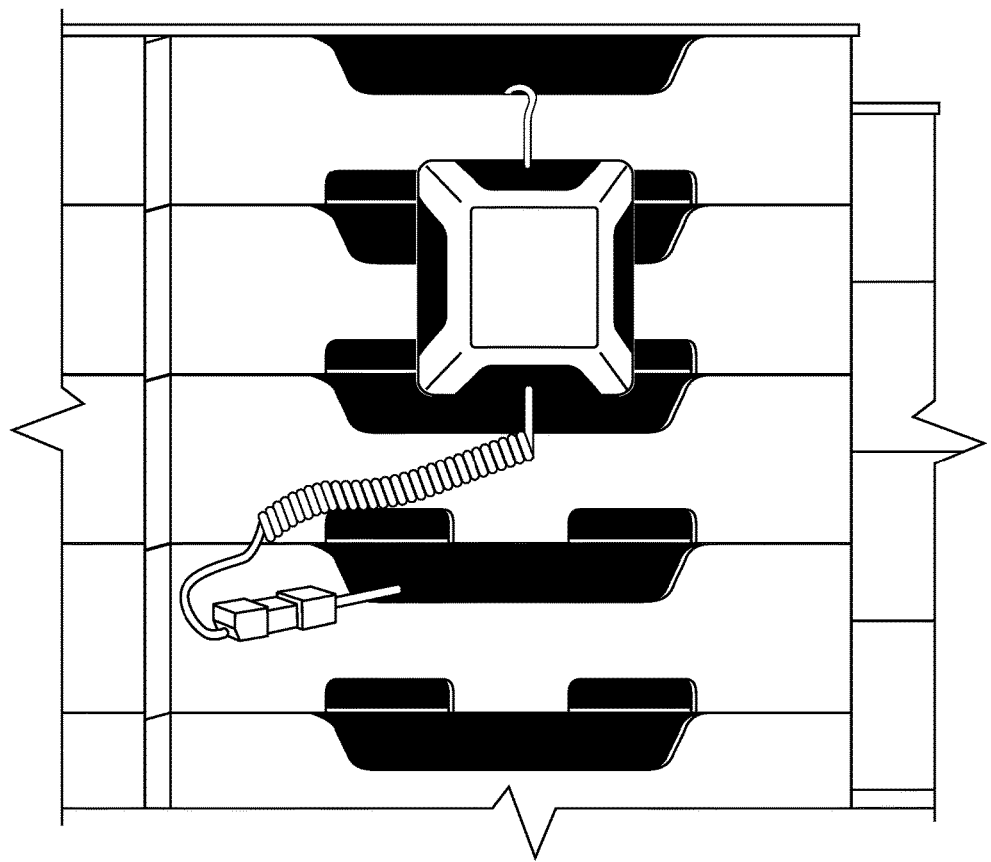
Figure 7C:
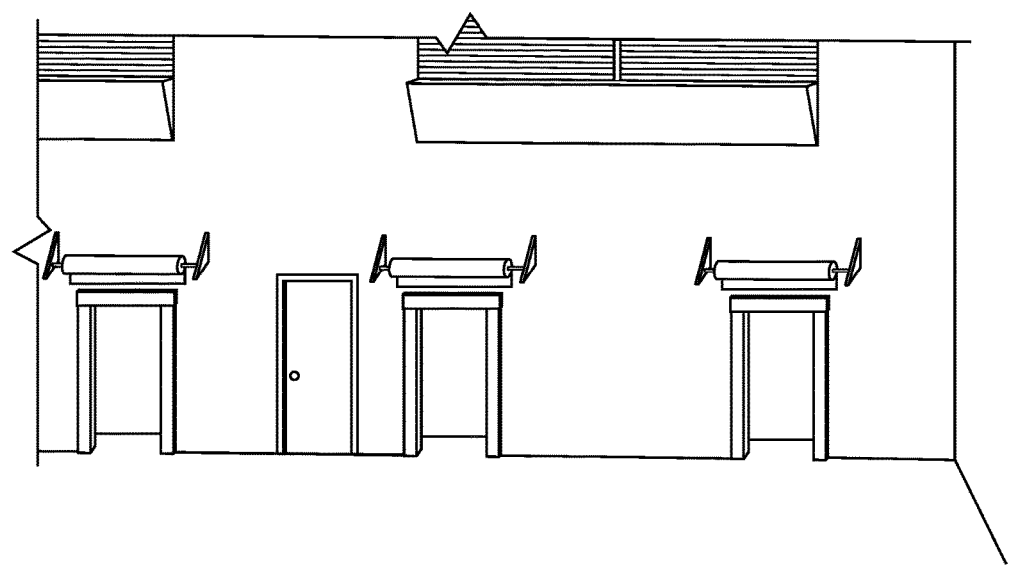
FIG. 7C illustrates pre-cooling facilities showing exhaust fans around which pallets are lined up on either side in two rows used in accordance with the present invention.
Figure 7D:
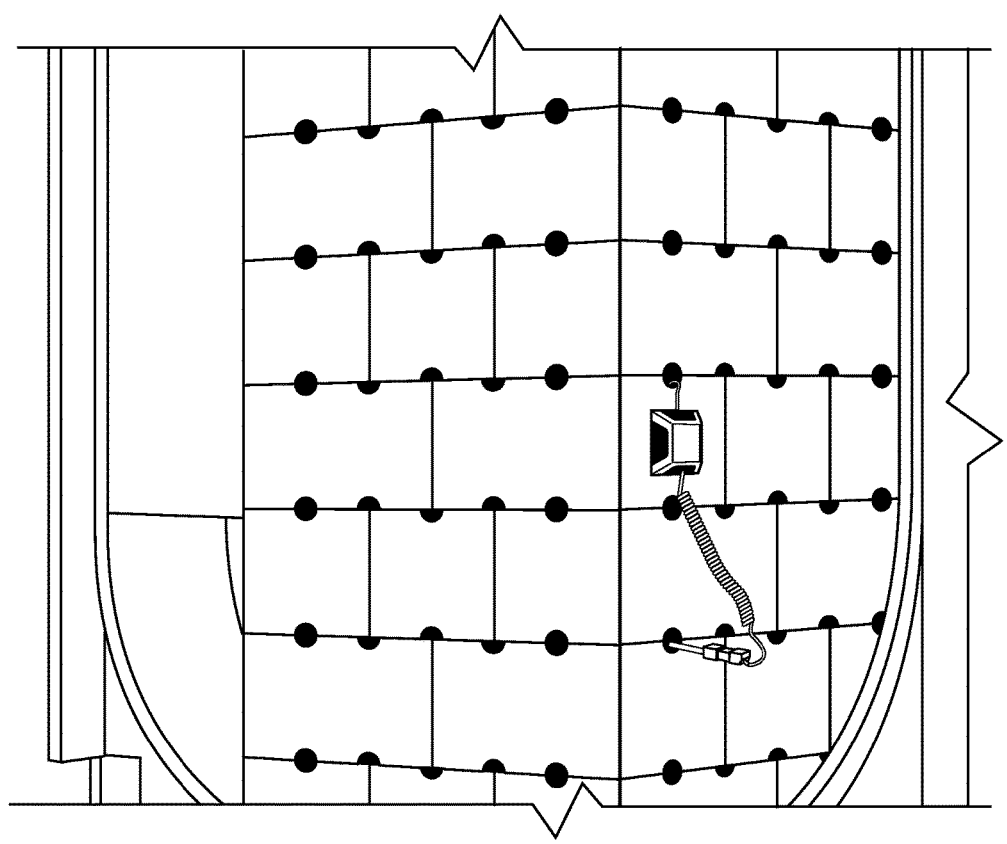
FIG. 7D depicts a pallet of food products having a temperature sensor mounted thereon in a vacuum tube cooling container according to the principles of the present invention.

FIG. 6 illustrates a pallet of food products being cooled through the use of a fan removing excess heat. FIGS. 7A and 7B illustrate pallets of food products having temperature sensors according to a preferred and non-limiting embodiment mounted thereon. FIG. 7C illustrates doors/entrances to vacuum cooling containers or facilities. FIG. 7D illustrates a pallet of food products in a vacuum tube cooling container.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system for monitoring temperature of food products, comprising:
a plurality of temperature sensors, each temperature sensor comprising at least one processor, a sensor probe adapted for insertion in a food product, and a wireless transmitter, each temperature sensor programmed or configured to sense temperature data for the food product, and wirelessly transmit the temperature data; and
at least one server computer configured to:
receive the temperature data wirelessly transmitted by each of the plurality of temperature sensors;
generate at least one graphical user interface based at least partially on the temperature data, the at least one graphical user interface comprising a visual representation of a plurality of cooling containers and a plurality of units of food products, the visual representation of the plurality of units of food products visually arranged within the visual representation of the plurality of cooling containers, wherein at least one representation of one cooling container of the plurality of cooling containers has a blank space based on spatial availability for at least one additional unit of food products, wherein each visual representation of each unit of food products of the plurality of units of food products comprises a color based at least partially on the temperature data corresponding to that unit of food product and wherein the visual representations of the units of food products are arranged to represent an actual position of each unit of food products relative to other units of food products within the same cooling container;
receive updated temperature data wirelessly transmitted by at least one temperature sensor of the plurality of temperature sensors corresponding to at least one unit of food products of the plurality of units of food products;
determine, based at least partially on the updated temperature data, that the at least one unit of food products should be moved out of at least one of the plurality of cooling containers; and
in response to determining that the at least one unit of food products should be moved out of the at least one of the plurality of cooling containers, change the color of the visual representation of the at least one unit of food products and update the visual representations of the units of food products to represent the actual position of each unit of food products relative to other units of food products within the same cooling container.

2. The system of claim 1, further comprising at least one range extending device configured to receive the temperature data from the plurality of temperature sensors and transmit the temperature sensor to the at least one server computer.

3. The system of claim 1, wherein the food product is at least one produce item of a plurality of produce items on a pallet, and wherein the pallet is located in at least one vacuum cooler or one forced air pre-cooler or similar cooling devices/facilities, transportation vehicle or retail store shelf.

4. The system of claim 1, wherein the temperature data comprises at least one of the following: a pulp-temperature of the food product, a humidity for at least one of the plurality of cooling containers or a facility storing the food product, a pressure measurement, a carbon dioxide measurement, an oxygen measurement, an ethylene measurement, a measurement of microbial elements, a measurement from an environmental parameter, or any combination thereof.

5. The system of claim 1, wherein the sensor probe of at least one of the plurality of temperature sensors comprises a needle puncture probe.

6. The system of claim 1, further comprising a network device programmed or configured to receive the temperature data from the plurality of temperature sensors and upload the temperature data to at least one database.

7. The system of claim 1, further comprising a protective housing containing the at least one processor and the wireless transmitter.

8. The system of claim 1, further comprising a connection arrangement attached to at least one of the plurality of temperature sensors.

9. The system of claim 1, wherein the at least one graphical user interface comprises at least one web page.

10. The system of claim 1, wherein the at least one graphical user interface displays at least one of a graph or a chart based on the temperature data over time.

11. The system of claim 1, wherein the at least one graphical user interface comprises an indication of a current stage that at least one of the plurality of cooling containers or at least one of the plurality of units of food products is in, and wherein the indication is generated automatically and without human interaction.

12. The system of claim 11, wherein the current stage is at least one stage of a plurality of possible stages and comprises at least one of the following: at least one unit of food products is ready to be moved or removed, at least one unit of food products will be ready to be moved or removed in a predefined period of time, a cooling rate should be changed, a temperature is above or below a required threshold temperature, or any combination thereof.

13. The system of claim 1, wherein the visual representation of each of the plurality of units of food products comprises a visual representation of at least one pallet located within the visual representation of a cooling container of the plurality of cooling containers.

14. The system of claim 13, wherein the visual representation of the at least one pallet comprises numerical data representing a current or recent temperature of a food product in the at least one pallet.

15. The system of claim 1, wherein the at least one graphical user interface comprises visual representations of vacuum tubes, tunnels and, within each tunnel, rows.

16. The system of claim 1, wherein the at least one server computer is configured to automatically turn off and/or turn on a cooling system in a cooling container housing the food products based at least partially on the temperature data.

17. The system of claim 1, wherein the color is determined based at least partially on the temperature data and specified ranges of temperatures, each range associated with a different color of a plurality of possible colors.

18. The system of claim 17, wherein at least one color of the plurality of possible colors indicates at least that the food product or the unit of food products needs to be switched over or moved from a pre-cooler to a cooler.

19. The system of claim 17, wherein the at least one user interface prompts a user, based at least partially on the temperature data and at least one predefined algorithm, to perform at least one of the following actions: remove sensors and swap pallets, remove sensors and move pallets, or any combination thereof.

20. The system of claim 1, wherein the at least one server computer is further configured to:
- determine when the food product, or a pallet containing the food product, has reached a predetermined temperature or is within a specified temperature range; and
- generate at least one alert when the specified temperature or temperature range has been reached.

21. The system of claim 20, wherein the at least one alert comprises at least one of the following: an email, a text message, an automated phone call, a push notification, or any combination thereof.

22. The system of claim 1, wherein at least one of the plurality of temperature sensors is configured to be calibrated remotely.

23. The system of claim 1, further comprising a protective housing containing the at least one processor and the wireless transmitter.

24. A computer-implemented method for monitoring food product temperatures, comprising:
- inserting at least one of a plurality of temperature sensors into a food product;
- receiving, from the plurality of temperature sensors, temperature data over a wireless network, wherein the temperature data comprises a pulp-temperature of the food product;
- storing the temperature data in at least one data structure; and
- generating data configured to display, on at least one user computer, a graphical user interface based at least partially on the temperature data, the at least one graphical user interface comprising a visual representation of a plurality of cooling containers and a plurality of units of food products, wherein each visual representation of each unit of food products of the plurality of food products comprises a color based at least partially on the temperature data corresponding to that unit of food product, wherein at least one representation of one cooling container of the plurality of cooling containers has a blank space based on spatial availability for at least one additional unit of food products, and wherein the visual representations of the units of food products are arranged to represent an actual position of each unit of food products relative to other units of food products within the same cooling container;
- receiving updated temperature data wirelessly transmitted by at least one temperature sensor of the plurality of temperature sensors corresponding to at least one unit of food products of the plurality of units of food products;
- determining, based at least partially on the updated temperature data, when the at least one unit of food products should be moved into or out of a cooling container; and
- in response to determining that the at least one unit of food products should be moved out of the at least one of the plurality of cooling containers: (i) changing the color of the visual representation of the at least one unit of food products, (ii) moving the at least one unit of food products out of the cooling container, and (iii) updating the visual representations of the units of food products to represent the actual position of each unit of food products relative to other units of food products within the same cooling container.

25. The computer-implemented method of claim 24, wherein the color is determined based at least partially on the temperature data and specified ranges of temperatures, each range associated with a different color of a plurality of possible colors.

26. The computer-implemented method of claim 24, further comprising:
- determining when the food product, or a pallet containing the food product, has reached a predetermined temperature or is within a specified temperature range; and
- generating at least one alert when the specified temperature or temperature range has been reached.

27. The system of claim 23, further comprising at least one attachment arrangement connected to the housing, the at least one attachment arrangement adapted to be attached to a package or pallet.

* * * * *